United States Patent
Kazama

[11] Patent Number: 5,897,571
[45] Date of Patent: Apr. 27, 1999

[54] FORCEPS

[76] Inventor: Shigeru Kazama, 2-6-3, Naruse, Machida-shi, Tokyo, Japan

[21] Appl. No.: 08/896,769
[22] Filed: Jul. 18, 1997

[30] Foreign Application Priority Data

Jul. 22, 1996 [JP] Japan .................................... 8-223020

[51] Int. Cl.$^6$ ...................................................... A61B 17/28
[52] U.S. Cl. .......................... 606/205; 606/210; 606/216; 606/208
[58] Field of Search .................................... 606/205, 133, 606/52, 51, 167, 211; 294/99.2

[56] References Cited

U.S. PATENT DOCUMENTS 979,697 12/1910 Prankard .................................. 606/133

*Primary Examiner*—Michael Buiz
*Assistant Examiner*—Tan-Uyen T. Ho
*Attorney, Agent, or Firm*—Thelen, Reid & Priest L.L.P.

[57] ABSTRACT

A forceps according to the invention can securely grasp a tissue or a part located in a deep and remote position and extending in parallel with the swinging direction of the handles. Additionally, it can be used without giving the user a strange feeling if he or she is accustomed to use known forcepses and is free from hygienic problems. It comprises a handle section having a first handle and a second handle coupled to each other to form a unitary member with a variable included angle, a fixed blade section fitted to the front end of the first handle and inclined toward the second handle, a swingable blade section arranged to pivot on a spot close to the root of the fixed blade section and a swing-link section for swingably linking a spot close to the front end of said second handle to the swingable blade section, the swingable blade section being moved to come closer to the fixed blade section by reducing the included angle between the first and second handles.

5 Claims, 2 Drawing Sheets

FORCEPS

BACKGROUND OF THE INVENTION

1. Field of the Invention

This invention relates to a forceps and, more particularly, it relates to a forceps adapted to seizing and holding a tissue located in a deep operating site of the body in a surgical operation that may be a cardiac surgical operation and also to grasping a part located in a deep and remote area of a precision machine.

2. Prior Art

Known forceps typically comprise a pair of forked handles and an associated pair of blades extending linearly from the respective handles and therefore it is practically impossible for such a forceps to grasp a tissue or a part located in a deep and narrow position, although it may be handled with each to grasp an object located in a broad area. To cope with this problem, there have been proposed forceps comprising a pair of forked handles and a pair of blades inclined in a direction that is perpendicular relative to the swinging direction of the handles.

A forceps comprising a pair of forked handles and a pair of blades inclined in a direction perpendicular relative to the swinging direction of the handles as described above is adapted to grasp a tissue or a part extending perpendicularly relative to the swinging direction of the handles but it cannot successfully be used to grasp an object extending in parallel with the swinging direction of the handles. Particularly, cardiovascular surgical operations are normally conducted in a deep and/or narrow operating site for any of the aortae or the cardiac valves and the use of such a forceps unadapted to grasping a tissue extending perpendicularly relative to the swinging direction of the handles is often obstructive and hazardous.

In view of the above identified problems of known forceps, it is therefore an object of the present invention to provide a forceps adapted to grasping a tissue or a part located in a deep and remote position and extending in parallel with the swinging direction of the handles.

Another object of the invention is to provide a forceps that can achieve the above identified object without giving the user a strange feeling if he or she is accustomed to use known forcepses as described above and is free from hygienic problems.

SUMMARY OF THE INVENTION

According to a first aspect of the invention, the above objects are achieved by providing a forceps comprising a handle section having a first handle and a second handle coupled to each other to form a unitary member with a variable included angle, a fixed blade section fitted to the front end of the first handle and inclined toward the second handle, a swingable blade section arranged to pivot on a spot close to the root of the fixed blade section and a swing-link section for swingably linking a spot close to the front end of said second handle to the swingable blade section, the swingable blade section being moved to come closer to the fixed blade section by reducing the included angle between the first and second handles.

According to a second aspect of the invention, there is provided a forceps comprising a handle section having a first handle and a second handle coupled to each other to form a unitary member with a variable included angle, a fixed blade section fitted to the front end of the first handle and inclined toward the second handle, a swingable blade section swingably arranged on a spot close to the root of the fixed blade section and urged to move away from said fixed blade to abut the second handle, the swingable blade section being moved to come closer to the fixed blade section by reducing the included angle between the first and second handles.

Preferably, said swingable blade section is fitted to said first handle by means of a leaf spring.

Thus, a forceps according to the invention can securely grasp a tissue or a part located in a deep and remote position and extending in parallel with the swinging direction of the handles.

Additionally, a forceps according to the invention can be used without giving the user a strange feeling if he or she is accustomed to use known forcepses as described above and is free from hygienic problems.

DETAILED DESCRIPTION OF THE PREFERRED EMBODIMENT

Figure 1:
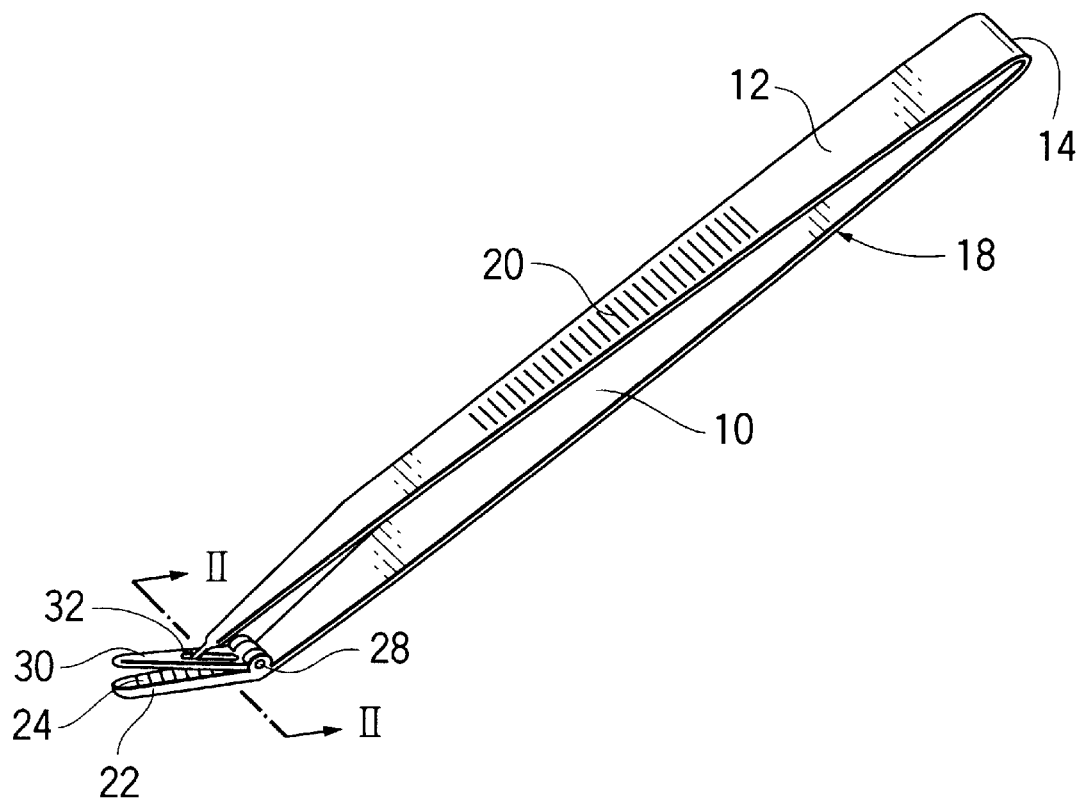
FIG. 1 is a schematic perspective view of a first embodiment of forceps according to the invention.

Referring to FIG. 1 showing a schematic perspective view of a first embodiment of forceps according to the invention, it comprises a handle section 18 formed as a unitary member by linking a first handle 10 and a second handle 12 at a coupling section 14 with a variable included angle. The first handle 10 and the second handle 12 are provided at respective middle sections of the outer surfaces thereof with a plurality of transversal anti-slip ridges 20.

Figure 2:
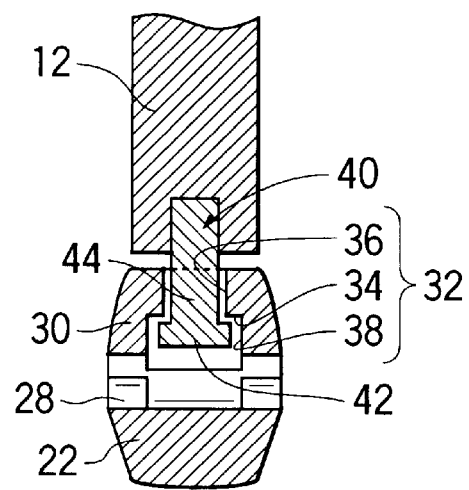
FIG. 2 is a schematic cross sectional view of the embodiment of FIG. 1 taken along line II—II.

A fixed blade section 22 is fitted to the front end of the first handle 10 and inclined toward the second handle 12 by an angle of 40° for example. A plurality of transversal ridges 24 are arranged on the inclined inner surface of the fixed blade section 22. A swingable blade 30 is extending from the front end of the first handle 10 toward the second handle 12 and arranged so as to pivot on a spot close to the root of the fixed blade section 22 by means of a hinge 28. A plurality of transversal ridges (not shown) are arranged on the side of the swingable blade 30 facing the fixed blade 22. As seen from FIGS. 1 and 2, the swingable blade 30 is provided with a sliding groove 32 extending along the radial swing plane of the swingable blade 30. The sliding groove 32 has a narrow groove section 36 and a wide groove section separated from each other to form a step 34.

A sliding projection 40 is partly buried into the front end of the second handle 12 and designed to slide in the sliding groove 32. The sliding projection 40 has a head section 42 engagedly held in the wide groove 38 and a support section supporting the head section 42 and engagedly held in the narrow groove 36. When the second handle 12 is free from any external force, the first handle 10 and the second handle 12 show an included angle of about 30°. The user can grasp an object with the first handle 10 and the second handle 12 by holding first handle 10 and the second handle 12 in a hand and applying a force to press the swingable blade 30 against the fixed blade section 22.

Figure 3:
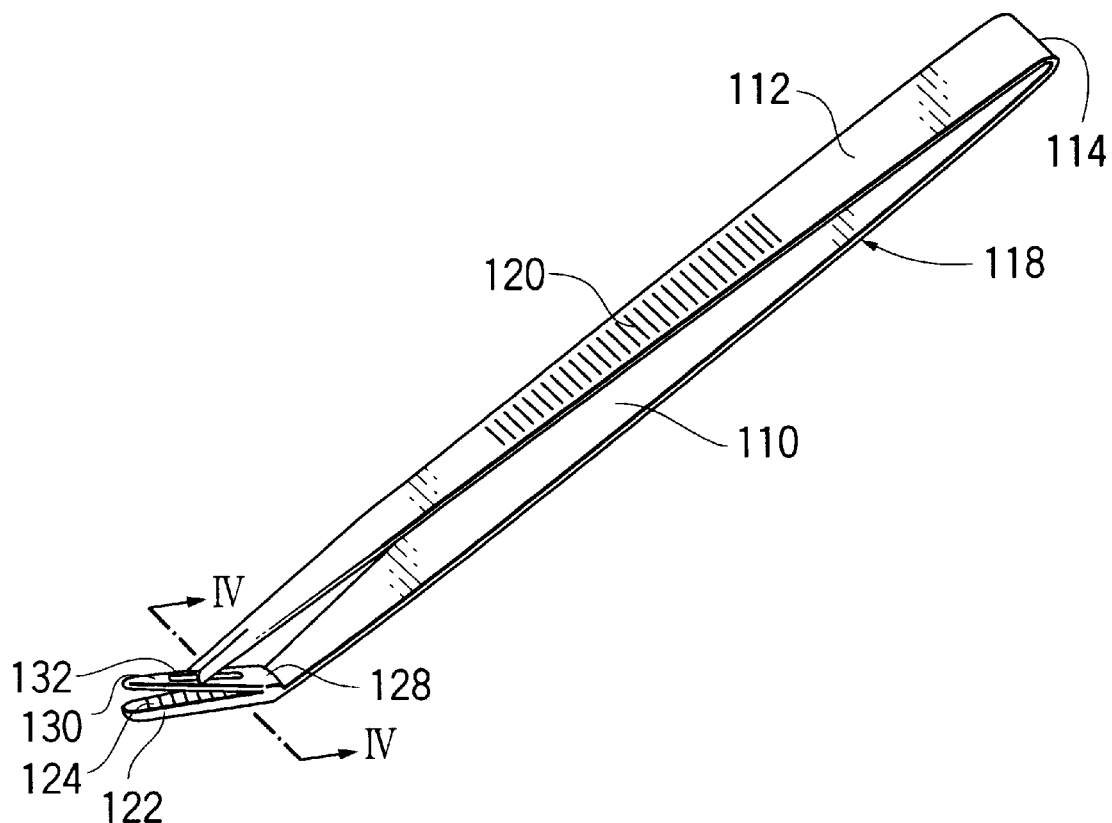
FIG. 3 is a schematic perspective view of a second embodiment of forceps according to the invention.

Referring now to FIG. 3, showing a schematic perspective view of a second embodiment of forceps according to the invention, it comprises a handle section 118 formed as a unitary member by linking a first handle 110 and a second handle 112 at a coupling section 114 with a variable included angle. The first handle 110 and the second handle 112 are provided at respective middle sections of the outer surfaces thereof with a plurality of transversal anti-slip ridges 120.

Figure 4:
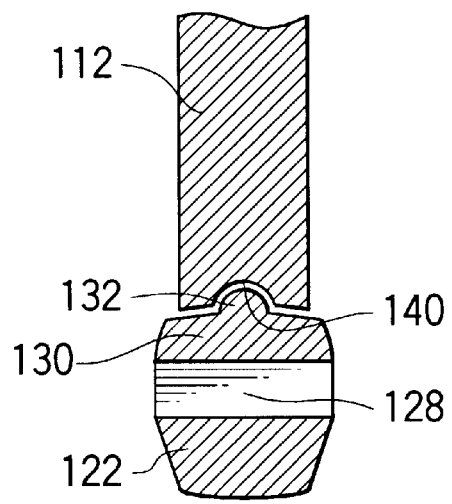
FIG. 4 is a schematic cross sectional view of the embodiment of FIG. 2 taken along line IV—IV.

A fixed blade section 122 is fitted to the front end of the first handle 110 and inclined toward the second handle 112 by an angle of 40° for example. A plurality of transversal ridges 124 are arranged on the inclined inner surface of the fixed blade section 122. A swingable blade 130 is extending from the front end of the first handle 110 toward the second handle 112 and arranged so as to pivot on a spot close to the root of the fixed blade section 122 and be urged to move away from the fixed blade section 122 by means of a leaf spring 128. A plurality of transversal ridges (not shown) are arranged on the side of the swingable blade 130 facing the fixed blade 122. As seen from FIGS. 3 and 4, the swingable blade 130 is provided on the side facing the second handle 112 with a guiding ridge 132 extending along the radial swing plane of the swingable blade 130.

The second handle 112 is provided on the front end thereof with a sliding groove 140 for engagedly receiving the guiding ridge 132. When the second handle 112 is free from any external force, the first handle 110 and the second handle 112 show an included angle of about 30°. The user can grasp an object with the first handle 110 and the second handle 112 by holding first handle 110 and the second handle 112 in a hand and applying a force to press the swingable blade 130 against the fixed blade section 122.

A forceps according to the invention may be entirely made of stainless steel or it may partly be made of synthetic resin for the purpose of insulation.

What is claimed is:

1. A forceps comprising a handle section having a first handle and a second handle coupled to each other to form a unitary member with a variable included angle, a fixed blade section fitted to the front end of the first handle and inclined toward the second handle, a swingable blade section arranged to pivot on a spot close to the root of the fixed blade section and a swing-link section for swingably linking a spot close to the front end of said second handle to the swingable blade section, the swingable blade section being moved to come closer to the fixed blade section by reducing the included angle between the first and second handles.

2. A forceps comprising a handle section having a first handle and a second handle coupled to each other to form a unitary member with a variable included angle, a fixed blade section fitted to the front end of the first handle and inclined toward the second handle, a swingable blade section swingably arranged on a spot close to the root of the fixed blade section and urged to move away from said fixed blade to abut the second handle, the swingable blade section being moved to come closer to the fixed blade section by reducing the included angle between the first and second handles.

3. A forceps according to claim 2, characterized in that said swingable blade section is fitted to said first handle by means of a leaf spring.

4. A forceps according to claim 1, wherein a spot close to the front end of the second handle is in sliding engagement with the swingable blade.

5. A forceps according to claim 2, wherein the front end of the second handle is in sliding engagement with the swingable blade.

* * * * *